US011883241B2

(12) United States Patent
Fujisawa

(10) Patent No.: US 11,883,241 B2
(45) Date of Patent: Jan. 30, 2024

(54) MEDICAL IMAGE DIAGNOSTIC APPARATUS, ULTRASONIC DIAGNOSTIC APPARATUS, MEDICAL IMAGING SYSTEM, AND IMAGING CONTROL METHOD

(71) Applicant: CANON MEDICAL SYSTEMS CORPORATION, Otawara (JP)

(72) Inventor: Yasuko Fujisawa, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/032,208

(22) Filed: Sep. 25, 2020

(65) Prior Publication Data

US 2021/0093303 A1 Apr. 1, 2021

(30) Foreign Application Priority Data

Sep. 30, 2019 (JP) ................................. 2019-179248
Sep. 18, 2020 (JP) ................................. 2020-157597

(51) Int. Cl.
*A61B 8/00* (2006.01)
*G06T 7/55* (2017.01)
*A61B 8/08* (2006.01)

(52) U.S. Cl.
CPC .............. *A61B 8/54* (2013.01); *A61B 8/085* (2013.01); *A61B 8/4461* (2013.01); *A61B 8/463* (2013.01); *A61B 8/466* (2013.01); *A61B 8/565* (2013.01); *G06T 7/55* (2017.01); *G06T 2207/10132* (2013.01)

(58) Field of Classification Search
CPC ......... A61B 8/54; A61B 8/085; A61B 8/4461; A61B 8/463; A61B 8/466; A61B 8/565; A61B 8/485; A61B 8/0825; A61B 8/4245; A61B 8/4416; A61B 8/4494; A61B 8/483; A61B 8/5207; A61B 8/5223; A61B 8/5246; A61B 8/5261; A61B 8/44; A61B 5/055; A61B 6/032; A61B 8/4444; A61B 8/481; A61B 8/488; A61B 8/5269; A61B 8/56; G06T 7/55; G06T 2207/10132

See application file for complete search history.

(56) References Cited

U.S. PATENT DOCUMENTS

| 6,126,599 A * | 10/2000 | Jago ..................... G01S 7/52025 600/443 |
| 6,213,945 B1 * | 4/2001 | Tynan .................... A61B 8/461 600/441 |
| 6,524,246 B1 * | 2/2003 | Kelly ..................... B82Y 15/00 600/437 |

(Continued)

FOREIGN PATENT DOCUMENTS

| JP | 2017-225544 A | 12/2017 | |
| WO | WO-2019148154 A1 * | 8/2019 | ............. A61B 34/10 |

*Primary Examiner* — Sanjay Cattungal
(74) *Attorney, Agent, or Firm* — Oblon, McClelland, Maier & Neustadt, L.L.P.

(57) ABSTRACT

The medical image diagnostic apparatus according to the embodiment includes processing circuitry. The processing circuitry is configured to acquire a medical image acquired by performing an imaging of a target in a subject and position data corresponding to the medical image. The processing circuitry is configured to determine, based on the acquired medical image and the acquired position data, an unimaged region of the target that is not included in the medical image.

19 Claims, 12 Drawing Sheets

(56) References Cited

U.S. PATENT DOCUMENTS

| | | | | |
|---|---|---|---|---|
| 7,645,238 B2* | 1/2010 | Hirsh | | A61B 8/4461 |
| | | | | 600/463 |
| 7,931,594 B2* | 4/2011 | Hirsh | | A61B 8/42 |
| | | | | 600/463 |
| 9,177,110 B1* | 11/2015 | Fram | | G06T 11/60 |
| 9,779,546 B2* | 10/2017 | Hunt | | G06T 17/20 |
| 9,852,272 B1* | 12/2017 | Fram | | G16H 10/40 |
| 2004/0225221 A1* | 11/2004 | Olsson | | A61B 8/5238 |
| | | | | 600/447 |
| 2004/0267122 A1* | 12/2004 | Nadadur | | A61B 8/467 |
| | | | | 600/440 |
| 2007/0016029 A1* | 1/2007 | Donaldson | | A61B 8/565 |
| | | | | 600/437 |
| 2009/0299182 A1* | 12/2009 | Asafusa | | A61B 8/481 |
| | | | | 600/458 |
| 2011/0311116 A1* | 12/2011 | Benn | | G06T 11/00 |
| | | | | 382/128 |
| 2012/0078097 A1* | 3/2012 | Wang | | A61B 8/0883 |
| | | | | 600/437 |
| 2013/0190600 A1* | 7/2013 | Gupta | | A61B 8/0866 |
| | | | | 600/407 |
| 2013/0345563 A1* | 12/2013 | Stuebe | | A61B 5/316 |
| | | | | 600/440 |
| 2015/0297177 A1* | 10/2015 | Boctor | | A61B 34/30 |
| | | | | 600/437 |
| 2015/0325036 A1* | 11/2015 | Lee | | A61B 8/54 |
| | | | | 600/437 |
| 2016/0081663 A1* | 3/2016 | Chen | | G06T 7/62 |
| | | | | 600/407 |
| 2016/0110632 A1* | 4/2016 | Kiraly | | G06T 7/11 |
| | | | | 382/128 |
| 2016/0173770 A1* | 6/2016 | Fosodeder | | A61B 8/5207 |
| | | | | 348/77 |
| 2016/0331345 A1* | 11/2016 | Kong | | A61B 8/5207 |
| 2016/0345936 A1* | 12/2016 | Cho | | G01S 7/52084 |
| 2017/0124701 A1* | 5/2017 | Liang | | G06T 7/11 |
| 2017/0148190 A1* | 5/2017 | Kim | | A61B 8/5292 |

* cited by examiner

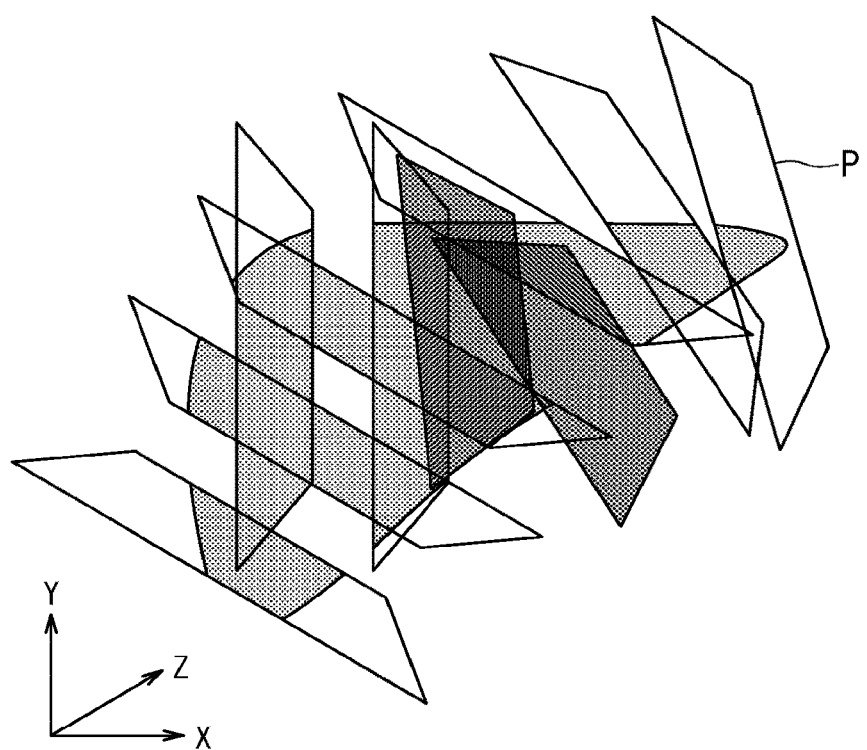
FIG. 11A
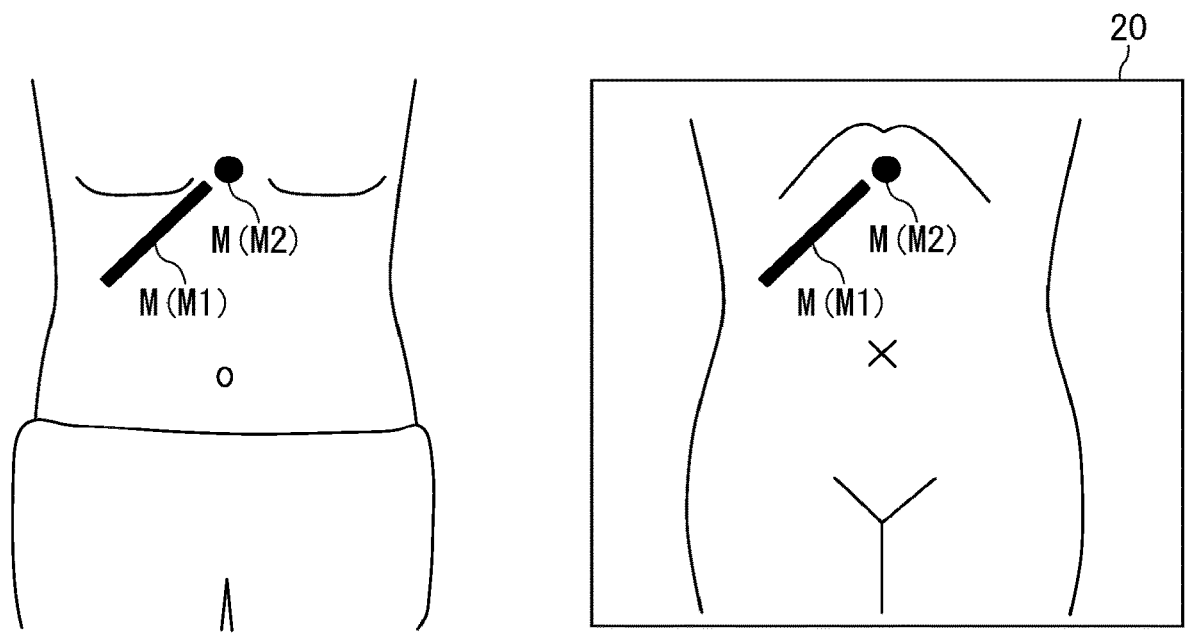
FIG. 11B
FIG. 11C

MEDICAL IMAGE DIAGNOSTIC APPARATUS, ULTRASONIC DIAGNOSTIC APPARATUS, MEDICAL IMAGING SYSTEM, AND IMAGING CONTROL METHOD

CROSS-REFERENCE TO RELATED APPLICATION

This application is based upon and claims the benefit of priority from Japanese Patent Application No. 2019-179248, filed on Sep. 30, 2019, and Japanese Patent Application No. 2020-157597, filed on Sep. 18, 2020, the entire contents of each of which are incorporated herein by reference.

FIELD

An embodiment disclosed in the specification and the like relates to a medical image diagnostic apparatus, an ultrasonic diagnostic apparatus, a medical imaging system, and an imaging control method.

BACKGROUND

There is a medical image diagnostic apparatus that generates medical image data in which a body tissue of a subject is imaged. Examples of the medical image diagnostic apparatus include an ultrasonic diagnostic apparatus, an X-ray computed tomography (CT) apparatus, and a magnetic resonance imaging (MRI) apparatus. The ultrasonic diagnostic apparatus transmits ultrasonic waves from an ultrasonic probe into the subject, generates echo signals based on reflected waves, and acquires a desired ultrasonic image by image processing. The X-ray CT apparatus generates a CT image such as an axial tomographic image of a subject based on electric signals based on X-rays detected by an X-ray detector by irradiating the subject with X-rays. The MRI apparatus is an apparatus that provides a static magnetic field for a subject and generates internal information of the subject as an MRI image based on high frequency pulses applied to the subject.

In the image acquisition by the medical image diagnostic apparatus, there is a case where only a part of the entire region of a target (for example, an organ) to be imaged in the subject is visualized. As a result, some data in the entire region to be imaged may be missing from the image. There is no problem if the data-missing area does not appear in the target region, but the data-missing area may appear in the target region. When the data-missing area appears in the target region, the data-missing area in the target region is an unimaged target region. In such a case, there is also a method of acquiring an unimaged target region by making up for the data-missing area with another image. However, there may be a case where there is no other image having no data-missing area, or the data-missing area is too large to make up for it.

Each of FIGS. 11A to 11C is a diagram showing a display example of information regarding the unimaged target region due to data-missing in the ultrasonic diagnostic apparatus as the example of the medical image diagnostic apparatus according to the embodiment.

Figure 12:
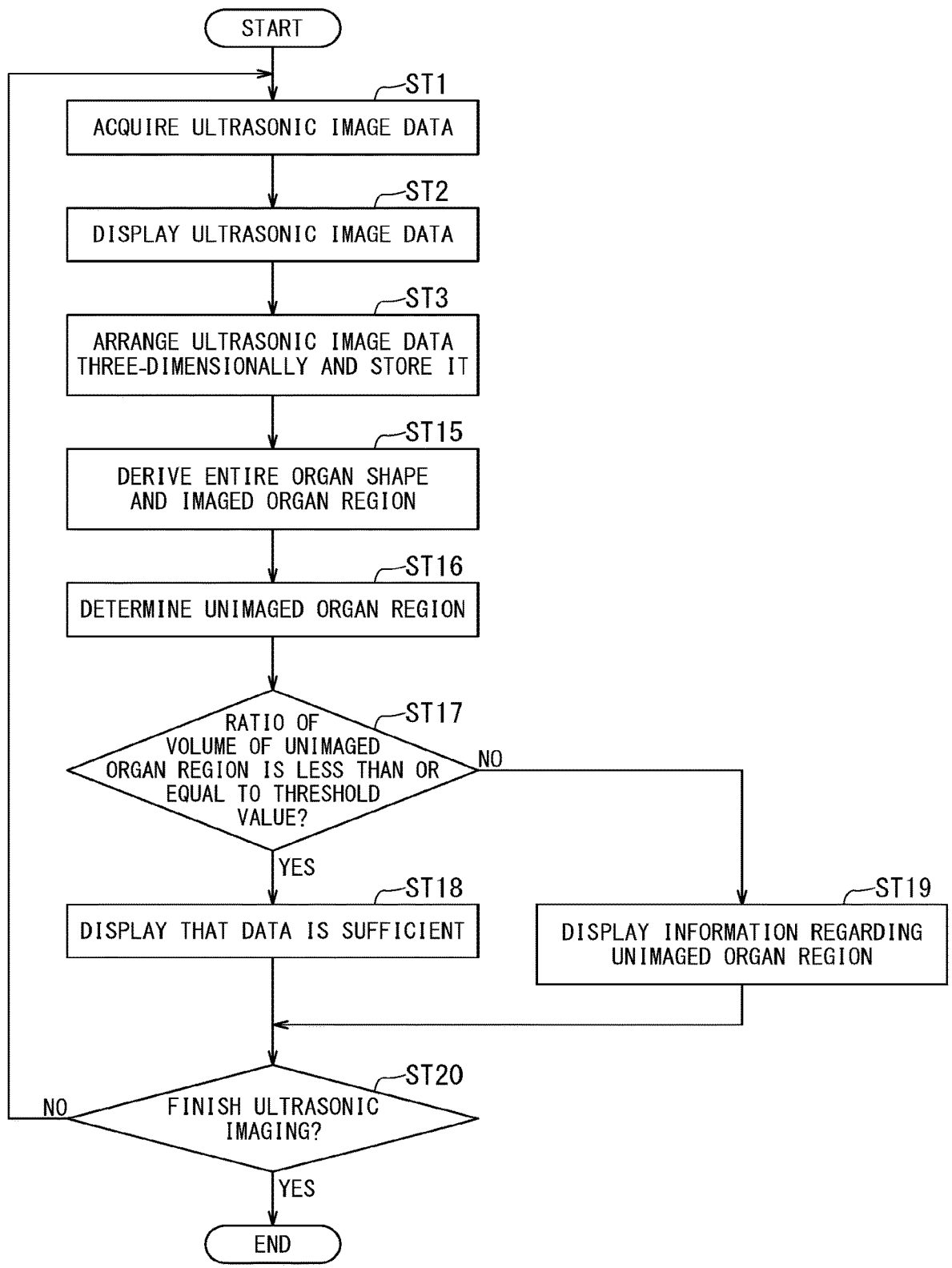

FIG. 12 is a diagram showing, as a flowchart, a second operation example of the ultrasonic diagnostic apparatus as the example of the medical image diagnostic apparatus according to the embodiment.

Figure 13:
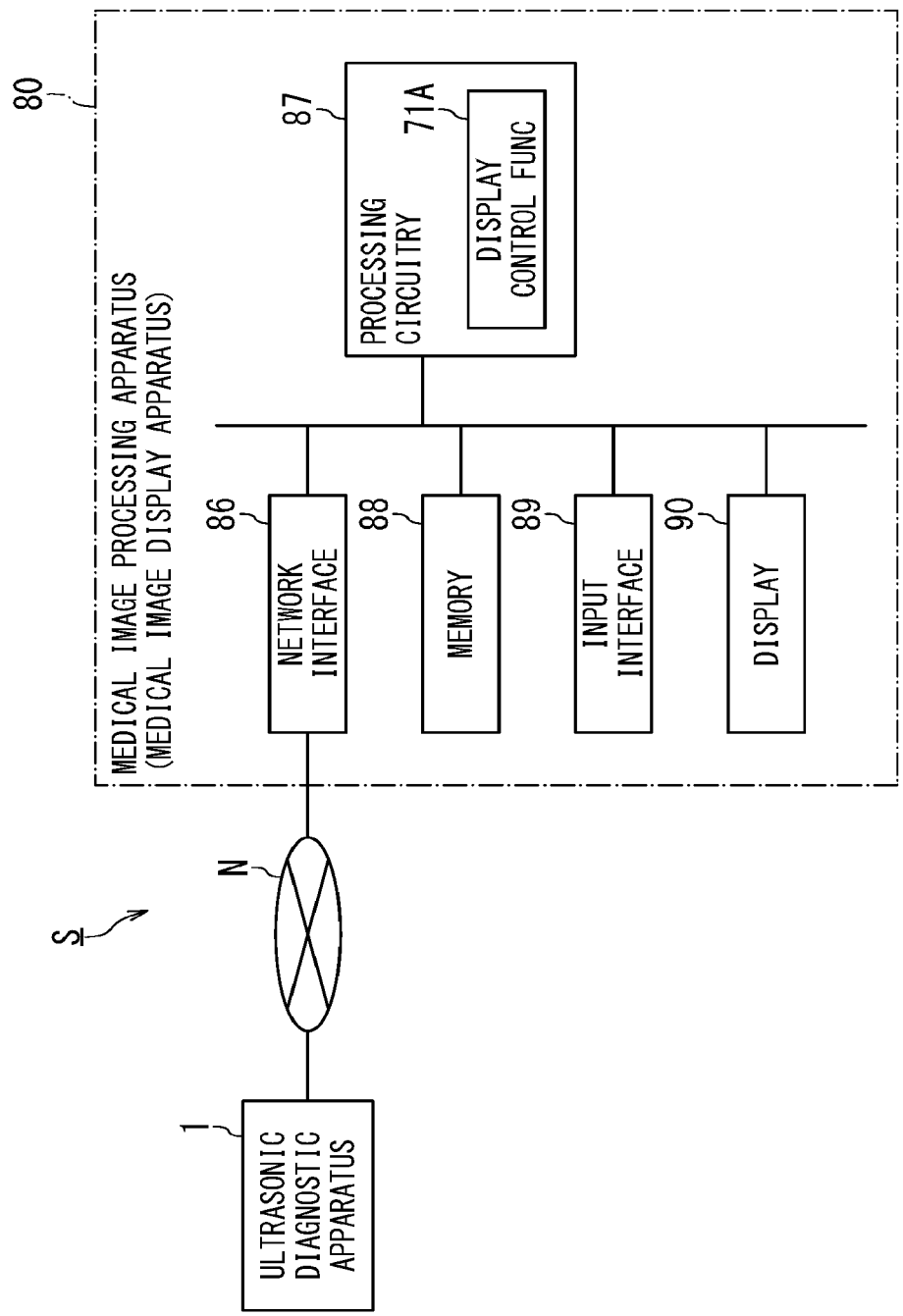

FIG. 13 is a schematic diagram showing a configuration of a medical image system including the ultrasonic diagnostic apparatus as an example of a medical image diagnostic apparatus according to the second modification.

DETAILED DESCRIPTION

A medical image diagnostic apparatus, an ultrasonic diagnostic apparatus, a medical imaging system, and an imaging control method according to an embodiment will be described with reference to the accompanying drawings.

The medical image diagnostic apparatus according to the embodiment includes processing circuitry. The processing circuitry is configured to acquire a medical image acquired by performing an imaging of a target in a subject and position data corresponding to the medical image. The processing circuitry is configured to determine, based on the acquired medical image and the acquired position data, an unimaged region of the target that is not included in the medical image.

Examples of the medical image diagnostic apparatus according to the embodiment include an ultrasonic diagnostic apparatus, an X-ray CT apparatus, and an MRI apparatus. The X-ray CT apparatus includes a scanner and a medical image processing apparatus. The X-ray CT apparatus detects X-rays by an X-ray detector by irradiating the subject with X-rays in the scanner, and generates an electric signal, thereby generates a CT image such as an axial tomographic image of the subject based on the received electric signals in the medical image processing apparatus. The MRI apparatus includes a scanner and a medical image processing apparatus. The MRI apparatus provides a static magnetic field formed by the scanner for a subject, applies a high-frequency pulse to the subject in the scanner, and receives MR signals, thereby generates an MRI image of the subject based on the MR signal in the medical image processing apparatus.

Hereinafter will be described as an example of an ultrasonic diagnostic apparatus as the medical image diagnostic apparatus, but not limited to that case.

1. Ultrasonic Diagnostic Apparatus

Figure 1:
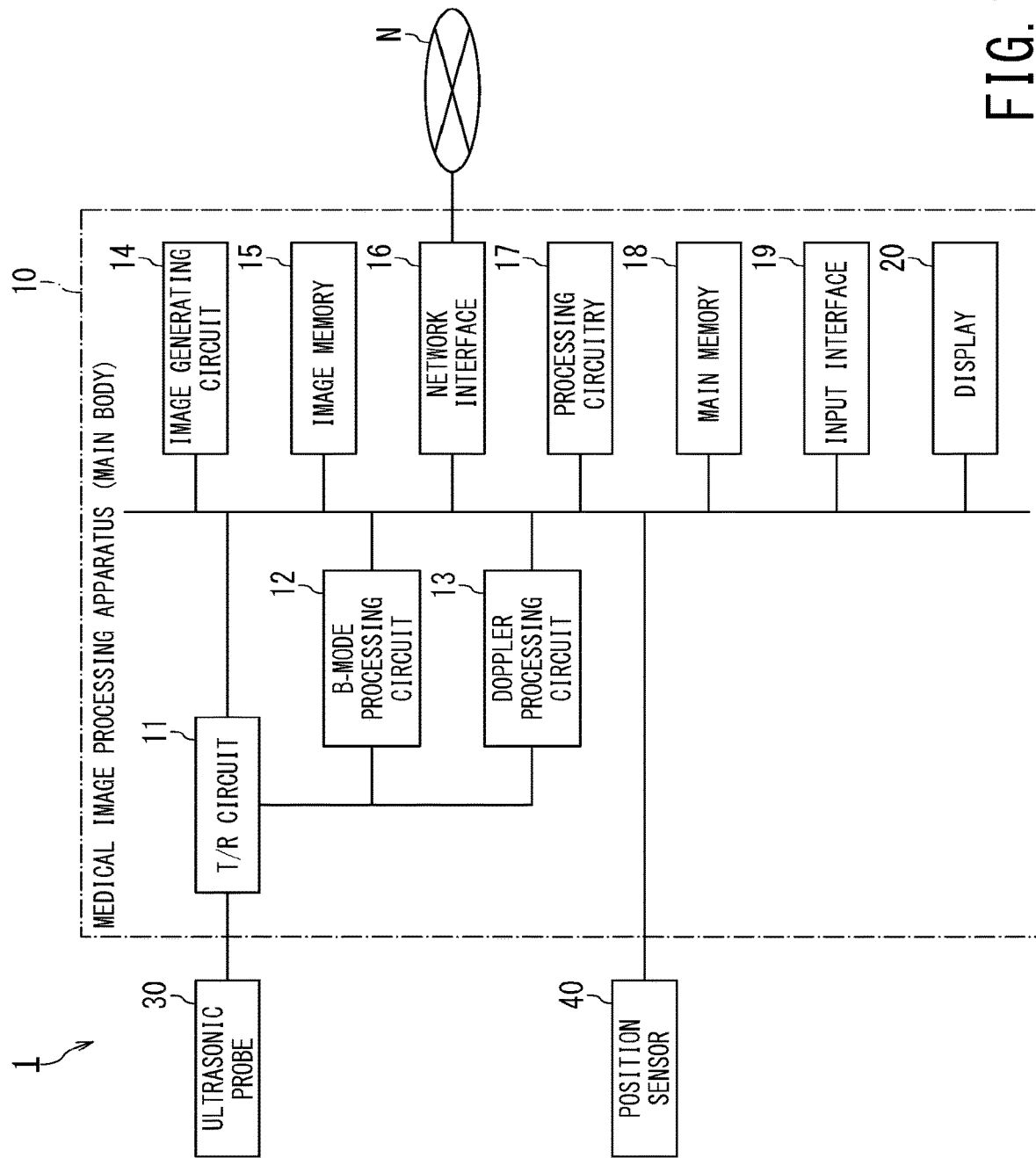
FIG. 1 is a schematic diagram showing a configuration of an ultrasonic diagnostic apparatus as an example of a medical image diagnostic apparatus according to an embodiment.

FIG. 1 is a schematic diagram showing a configuration of an ultrasonic diagnostic apparatus as an example of a medical image diagnostic apparatus according to an embodiment.

FIG. 1 shows an ultrasonic diagnostic apparatus 1 as an example of a medical image diagnostic apparatus according to an embodiment. The ultrasonic diagnostic apparatus 1 includes a main body 10 as a medical image processing apparatus, an ultrasonic probe 30 as a scanner, and a position sensor 40. In addition, not only the main body 10 may be referred to as an "ultrasonic diagnostic apparatus", the main body 10 and at least one of the ultrasonic probe 30 and the position sensor 40 may also be referred to as an "ultrasonic diagnostic apparatus". In the following description, the case where the ultrasonic diagnostic apparatus 1 includes both the ultrasonic probe 30 and the position sensor 40 in addition to the main body 10 will be described.

The main body 10 of the ultrasonic diagnostic apparatus 1 includes a transmission/reception (T/R) circuit 11, a B-mode processing circuit 12, a Doppler processing circuit 13, an image generating circuit 14, an image memory 15, a network interface 16, processing circuitry 17, a main memory 18, an input interface 19, and a display 20. The input interface 19 and the display 20 may be provided outside the main body 10 or may be provided outside the ultrasonic diagnostic apparatus 1. The circuits 11 to 14 are configured by application specific integrated circuits (ASIC) or the like. However, the invention is not limited to this case, and all or part of the functions of the circuits 11 to 14 may be realized by the processing circuitry 17 executing a computer program.

The T/R circuit 11 has a transmitting circuit and a receiving circuit (not shown). Under the control of the processing circuitry 17, the T/R circuit 11 controls transmission directivity and reception directivity in transmission and reception of ultrasonic waves. The case where the T/R circuit 11 is provided in the main body 10 will be described, but the T/R circuit 11 may be provided in the ultrasonic probe 30, or may be provided in both of the main body 10 and the ultrasonic probe 30. The T/R circuit 11 is one example of a transmitter-and-receiver.

The transmitting circuit has a pulse generating circuit, a transmission delay circuit, a pulsar circuit, etc., and supplies drive signals to ultrasonic transducers. The pulse generating circuit repeatedly generates rate pulses for forming transmission ultrasonic waves at a predetermined rate frequency. The transmission delay circuit gives a delay time to each rate pulse generated by the pulse generating circuit. The delay time for each transmission ultrasonic is necessary for focusing ultrasonic waves generated from the ultrasonic transducers of the ultrasonic probe 30 into one beam and determining the transmission directivity. In addition, the pulsar circuit applies the drive pulses to the ultrasonic transducers at timings based on the rate pulses. The transmission delay circuit arbitrarily adjusts the transmission direction of the ultrasonic beam transmitted from a piezoelectric transducer surface by changing the delay time given to each rate pulse.

The receiving circuit includes an amplifier circuit, an analog to digital (A/D) converter, an adder, and the like. The receiving circuit receives echo signals received by the ultrasonic transducers and performs various processes on the echo signals to generate echo data. The amplifier circuit amplifies the echo signals for each channel and performs the gain correction processing. The A/D converter performs A/D conversion of the gain-corrected echo signals, and gives a delay time necessary for determining reception directivity to digital data. The adder performs the addition processing on the echo signals processed by the A/D converter to generate echo data. With the addition processing of the adder, the reflection component from the direction corresponding to each reception directivity of the echo signals is emphasized.

Under the control of the processing circuitry 17, the B-mode processing circuit 12 receives the echo data from the receiving circuit, performs logarithmic amplification, envelope detection processing and the like, thereby generate data (two-dimensional (2D) or three-dimensional (3D) data) which signal intensity is presented by brightness of luminance. This data is generally called "B-mode data". The B-mode processing circuit 12 is one example of a B-mode processer.

The B-mode processing circuit 12 may change the frequency band to be visualized by changing the detection frequency using filtering processing. By using the filtering processing function of the B-mode processing circuit 12, harmonic imaging such as the contrast harmonic imaging (CHI) or the tissue harmonic imaging (THI) is performed. That is, the B-mode processing circuit 12 may separate the reflected wave data into harmonic data (or sub-frequency data) and fundamental wave data in a subject into which the contrast agent is injected. The harmonic data (or sub-frequency data) corresponds to reflected wave data with a harmonic component whose reflection source is the contrast agent (microbubbles or bubbles) in the subject. The fundamental wave data corresponds to reflected wave data with a fundamental wave component whose reflection source is tissue in the subject. The B-mode processing circuit 12 generates B-mode data for generating contrast image data based on the reflected wave data (reception signals) with the harmonic component, and generates B-mode data for generating fundamental wave image data based on the reflected wave data (reception signals) with the fundamental wave component.

Further, in the THI by using the filter processing function of the B-mode processing circuit 12, it is possible to separate the harmonic data or the sub-frequency data from the reflected wave data of the subject. The harmonic data or the sub-frequency data is reflected wave data (received signals) with a harmonic component. Then, the B-mode processing circuit 12 can generate B-mode data for generating the tissue image data based on the reflected wave data (received signals) with the harmonic component from which the noise component is removed.

Further, when performing the CHI or THI harmonic imaging, the B-mode processing circuit 12 can extract the harmonic component by a method different from the method using the above-described filter processing. In harmonic imaging, the amplitude modulation (AM: Amplitude Modulation) method, the phase modulation (PM: Phase Modulation) method, or an imaging method called the AM-PM method, which is a combination of the AM method and the PM method, is performed. In the AM method, the PM method, and the AMPM method, ultrasonic waves having different amplitudes and phases are transmitted a plurality of times with respect to the same scanning line. As a result, the T/R circuit 11 generates and outputs multiple reflected wave data (received signals) on each scanning line. Then, the B-mode processing circuit 12 extracts harmonic components by subjecting the multiple reflected wave data (received signals) of each scanning line to addition/subtraction processing according to the modulation method. Then, the B-mode processing circuit 12 performs envelope detection processing or the like on the reflected wave data (received signals) with the harmonic component to generate the B-mode data.

For example, when the PM method is performed, the T/R circuit 11 causes the scanning lines set by the processing circuitry 17 to transmit one set of ultrasonic wave having an inverted phase polarity, such as (−1, 1), with the same amplitude on each scanning line. Then, the T/R circuit 11 generates a reception signal by transmission of "−1" and a reception signal by transmission of "1", and the B-mode processing circuit 12 adds these two reception signals. As a result, the fundamental wave component is removed, and a signal in which the second harmonic component is mainly left is generated. Then, the B-mode processing circuit 12 performs envelope detection processing or the like on this signal to generate B-mode data regarding the THI or CHI.

Alternatively, for example, in the THI, a method of performing visualization using a second harmonic component and a difference tone component included in a received signal is put into practical use. In the visualization method using the difference sound component, for example, a transmission ultrasonic wave having a composite waveform is transmitted from the ultrasonic probe 30. The composite waveform is a composition of a first fundamental wave having a center frequency of "f1" and a second fundamental wave having a center frequency of "f2" with a center frequency higher than "f1". This combined waveform is a waveform acquired by combining the waveform of the first fundamental wave and the waveform of the second fundamental wave which phases are adjusted with each other such that a difference tone component having the same polarity as the second harmonic component is generated. The T/R circuit 11 transmits the transmission ultrasonic wave of the composite waveform, e.g. twice, while inverting the phase. In such a case, for example, the B-mode processing circuit 12 adds the two received signals to remove the fundamental wave component, extracts the harmonic component in which the difference tone component, and the second harmonic component are mainly left, and performs envelope detection processing and the like.

Under the control of the processing circuitry 17, the Doppler processing circuit 13 frequency-analyzes the phase information from the echo data from the receiving circuit, thereby generating data (2D or 3D data) acquired by extracting multiple dynamic data of moving target such as average speed, dispersion, power and the like. This data is generally called "Doppler data". In the embodiment, the moving target refers to, for example, blood flow, tissue such as heart wall, or contrast agent. The Doppler processing circuit 13 is one example of a Doppler processer.

Under the control of the processing circuitry 17, the image generating circuit 14 generates an ultrasonic image as image data presented in a predetermined luminance range based on the reception signals received by the ultrasonic probe 30. For example, the image generating circuit 14 generates, as the ultrasonic image, a B-mode image in which the intensity of the reflected wave is presented by luminance based on 2D B-mode data generated by the B-mode processing circuit 12. In addition, the image generating circuit 14 generates, as the ultrasonic image, a color Doppler image based on 2D Doppler data generated by the Doppler processing circuit 13. The color Doppler image includes an average speed image presenting moving state information, a dispersion image, a power image, or a combination image thereof. The image generating circuit 14 is one example of an image generator.

In the embodiment, the image generating circuit 14 generally converts (scan-converts) a scanning line signal sequence of ultrasonic scanning into a scanning line signal sequence of a video format for a television or the like, and generates ultrasonic image data for display. Specifically, the image generating circuit 14 generates the ultrasonic image data for display by performing coordinate conversion according to the ultrasonic scanning mode of the ultrasonic probe 30. The image generating circuit 14 performs various image processes other than the scan conversion. For example, the image generating circuit 14 performs image processing (smoothing processing) for regenerating an average luminance image using multiple image frames after scan conversion, or image processing using a differential filter in the image (processing for enhancing edges) and the like. Further, the image generating circuit 14 combines character information of various parameters, scales, body marks, and the like with the ultrasonic image data.

That is, the B-mode data and the Doppler data are the ultrasonic image data before the scan conversion processing. The data generated by the image generating circuit 14 is the ultrasonic image data for display after the scan conversion processing. The B-mode data and the Doppler data are also called raw data. The image generating circuit 14 generates 2D ultrasonic image data for display based on the 2D ultrasonic image data before the scan conversion processing.

The image memory 15 includes multiple memory cells in one frame in two axial directions, and includes a 2D memory which is a memory provided with multiple frames. The image memory 15, as the 2D memory, stores one frame or multiple frames of the ultrasonic image as 2D image data generated by the image generating circuit 14 under the control of the processing circuitry 17. The image memory 15 is one example of a storage.

Further, the image generating circuit 14 performs coordinate conversion on the 3D B-mode data generated by the B-mode processing circuit 12, thereby generates 3D B-mode image data. The image generating circuit 14 also performs coordinate conversion on the 3D Doppler data generated by the Doppler processing circuit 13, thereby generates 3D Doppler image data. The image generating circuit 14 generates "3D B-mode image data or 3D Doppler image data" as "3D ultrasonic image data (volume data)".

The image memory 15 may include a 3D memory which is a memory having multiple memory cells in three axis directions (X-axis, Y-axis, and Z-axis directions). The image memory 15, as the 3D memory, stores the multiple ultrasonic images generated by the image generating circuit 14 as the volume data under the control of the processing circuitry 17.

Then, in order to generate various 2D image data so as to display the volume data stored in the 3D memory on the display 20, the image generating circuit 14 performs processing for displaying the volume data on the 2D display and processing for displaying the 3D data three-dimensionally, with respect to the volume data. The image generating circuit 14 performs the processing such as volume rendering (VR) processing, surface rendering (SR) processing, MIP (Maximum Intensity Projection) processing, MPR (Multi Planer Reconstruction) processing, etc.

The network interface 16 implements various information communication protocols according to the network form. The network interface 16 connects the ultrasonic diagnostic apparatus 1 and other devices such as an external medical image managing apparatus and a medical image processing apparatus according to these various protocols. An electrical connection or the like via an electronic network is applied to this connection. In the embodiment, the electronic network generally refers to an information communication network using telecommunications technology. The electronic network includes a wired/wireless hospital backbone local area network (LAN) and the internet network, as well as a telephone communication line network, an optical fiber communication network, a cable communication network, a satellite communication network, or the like.

Further, the network interface 16 may implement various protocols for non-contact wireless communication. In this case, the main body 10 can directly transmit/receive data to/from the ultrasonic probe 30, for example, without going through the network. The network interface 16 is one example of a network connector.

The processing circuitry 17 may refer to a dedicated or general-purpose central processing unit (CPU), microprocessor unit (MPU), graphics processing unit (GPU), or the like. The processing circuitry 17 may refers to an ASIC, a programmable logic device, or the like. The programmable logic device is, for example, a simple programmable logic device (SPLD), a complex programmable logic device (CPLD), and a field programmable gate array (FPGA).

Further, the processing circuitry 17 may be constituted by a single circuit or a combination of independent circuit elements. In the latter case, the main memory 18 may be provided individually for each circuit element, or a single main memory 18 may store programs corresponding to the functions of the circuit elements. The processing circuitry 17 is one example of a processor.

The main memory 18 is constituted by a semiconductor memory element such as a random-access memory (RAM), a flash memory, a hard disk, an optical disk, or the like. The main memory 18 may be constituted by a portable medium such as a universal serial bus (USB) memory and a digital video disk (DVD). The main memory 18 stores various processing programs (including an operating system (OS) and the like besides the application program) used in the processing circuitry 17 and data necessary for executing the programs. In addition, the OS may include a graphical user interface (GUI) which allows the operator to frequently use graphics to display information on the display 20 to the operator and can perform basic operations by the input interface 19. The main memory 18 is one example of a storage.

The input interface 19 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 19 generates an input signal corresponding to the operation and outputs it to the processing circuitry 17. The input interface 19 is one example of an input unit.

The display 20 is constituted by a general display output device such as a liquid crystal display or an organic light emitting diode (OLED) display. The display 20 displays various kinds of information under the control of the processing circuitry 17. The display 20 is one example of a display unit.

The ultrasonic probe 30 of the ultrasonic diagnostic apparatus 1 is a scanner including minute transducers (piezoelectric elements) on the front surface. The ultrasonic probe 30 transmits/receives ultrasonic waves to/from a target in a subject (for example, a patient). Each transducer is an electroacoustic conversion element, and converts electric pulses into ultrasonic pulses during transmission. Further, the ultrasonic probe 30 has a function of converting reflected waves into electric signals (received signals) at the time of reception. The ultrasonic probe 30 is small and lightweight, and is connected to the main body 10 via a cable (or wireless communication).

The ultrasonic probe 30 is classified into types such as a linear type, a convex type, a sector type, etc. depending on differences in scanning system. Further, the ultrasonic probe 30 is classified into a 1D array probe in which transducers are arrayed in a one-dimensional (1D) manner in the azimuth direction, and a 2D array probe in which transducers are arrayed in a 2D manner in the azimuth direction and in the elevation direction, depending on the array arrangement dimension. The 1D array probe includes a probe in which a small number of transducers are arranged in the elevation direction.

In the embodiment, when performing 3D scanning, that is, volume scanning, a 2D array probe having a scanning method such as a linear type, a convex type, or a sector type is used as the ultrasonic probe 30. Alternatively, when the volume scan is performed, a 1D probe having a scan method such as a linear type, a convex type, or a sector type and having a mechanism that mechanically swings in the elevation direction is used as the ultrasonic probe 30. The latter probe is also called a mechanical 4D probe.

The position sensor 40 detects multiple position data of the ultrasonic probe 30 in time series and outputs the multiple position data to the main body 10. The position sensor 40 includes a sensor attached to the ultrasonic probe 30 and a sensor provided separately from the ultrasonic probe 30. The latter sensor is an optical sensor that images characteristic points of the ultrasonic probe 30 as a measurement target from multiple positions, and detects each position of the ultrasonic probe 30 on the principle of triangulation.

The type of the position sensor 40 attached to the ultrasonic probe 30 detects position data of itself, and outputs the position data to the main body 10. The position data of the position sensor 40 can also be regarded as the position data of the ultrasonic probe 30. The position data of the ultrasonic probe 30 includes a coordinate (X, Y, Z) of the ultrasonic probe 30 and a tilt angle (posture) from each axis. For example, the posture of the ultrasonic probe 30 can be detected by a magnetic field transmitter (not shown) sequentially transmitting triaxial magnetic fields while the position sensor 40 sequentially receiving the magnetic fields.

Further, the position sensor 40 may be a so-called nine-axis sensor. The nine-axis sensor includes at least one of: a three-axis gyro sensor that detects three-axis angular velocity in a 3D space; a three-axis acceleration sensor that detects three-axis acceleration in a 3D space; and a three-axis geomagnetic sensor that detects three-axis geomagnetism in a 3D space. The position sensor 40 is not an essential component.

Figure 2:
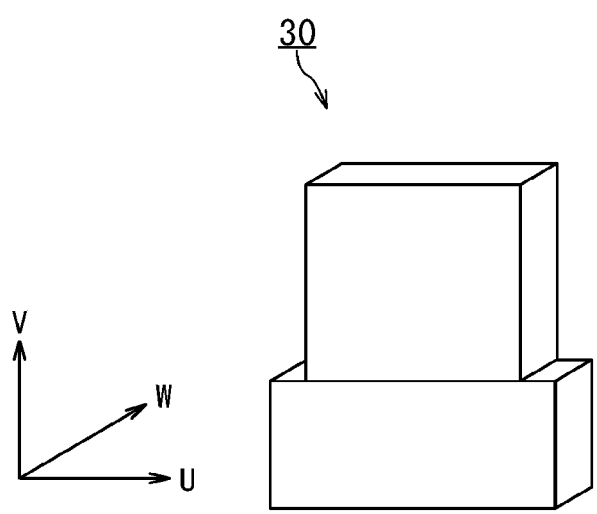
FIG. 2 is a diagram for explaining position data of an ultrasonic probe in the ultrasonic diagnostic apparatus as the example of the medical image diagnostic apparatus according to the embodiment.

FIG. 2 is a diagram for explaining position data of the ultrasonic probe 30.

FIG. 2 shows three orthogonal directions with respect to the ultrasonic probe 30, that is, the U-axis direction, the V-axis direction, and the W-axis direction. The U-axis direction is defined as the transducer array direction, that is, an azimuth direction. The V-axis direction is defined by the depth direction, that is, the direction orthogonal to the U-axis direction and the W-axis direction. The W-axis direction is defined as an elevation direction. Regarding the ultrasonic probe 30 which coordinate and posture are defined by the U-axis direction, the V-axis direction, and the W-axis direction. The ultrasonic probe 30 is arranged and operated to move arbitrarily in the XYZ space in which the subject is provided.

Subsequently, functions of the ultrasonic diagnostic apparatus 1 will be described.

Figure 3:
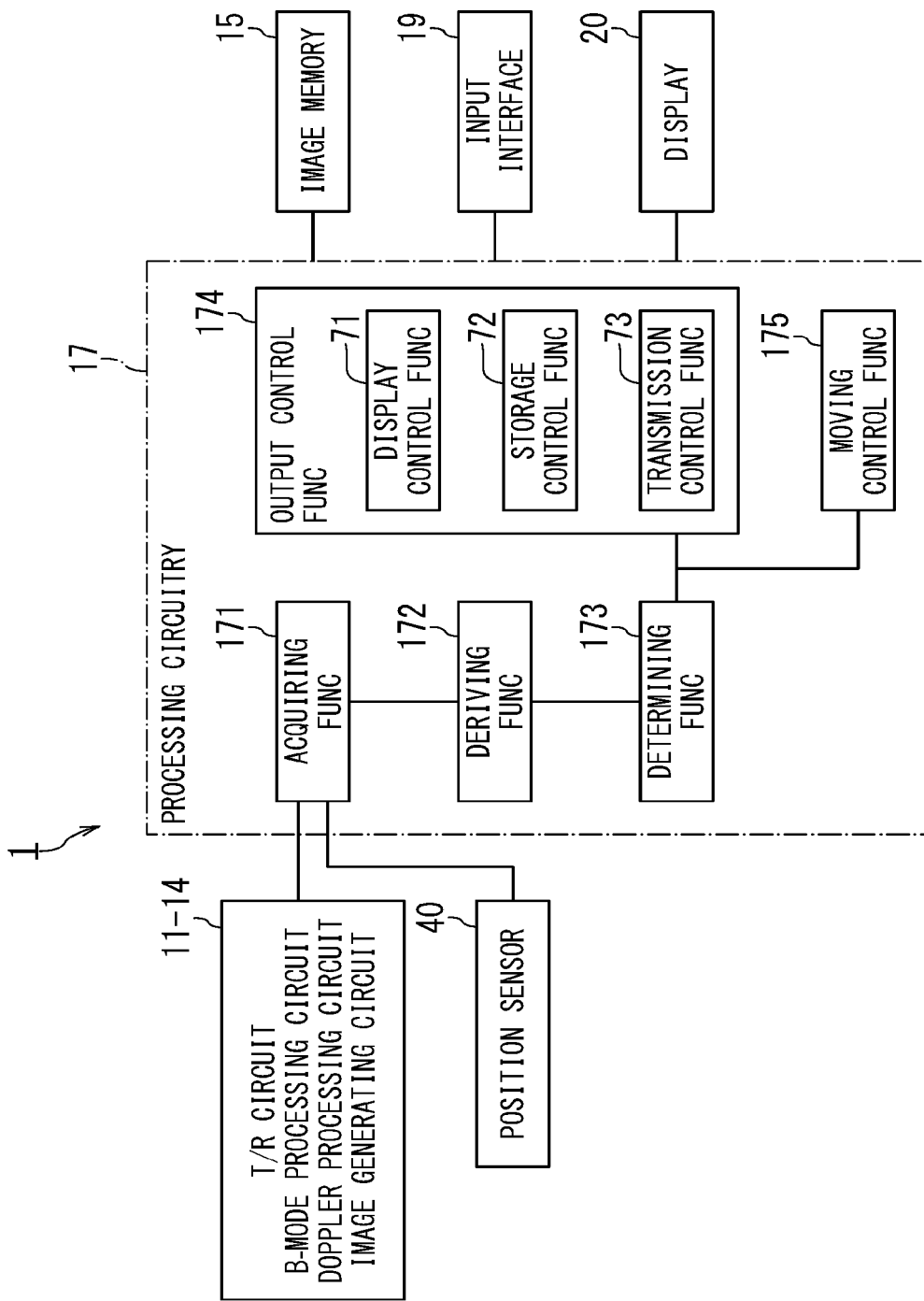
FIG. 3 is a block diagram showing functions of the ultrasonic diagnostic apparatus according to the embodiment.

FIG. 3 is a block diagram showing functions of the ultrasonic diagnostic apparatus 1.

The processing circuitry 17 reads and executes a computer program stored in the main memory 18 or directly incorporated in the processing circuitry 17, thereby realizes an acquiring function 171, a deriving function 172, a determining function 173, an output control function 174, and a moving control function 175. Hereinafter, a case where the functions 171 to 175 function as software will be described as an example. However, all or a part of the functions 171 to 175 may be provided in the ultrasonic diagnostic apparatus 1 as a circuit such as the ASIC. All or part of the deriving function 172 and the determining function 173 may be realized by an external apparatus connected via the network N.

The acquiring function 171 has a function of controlling the T/R circuit 11, the B-mode processing circuit 12, the Doppler processing circuit 13, the image generating circuit 14, and the like to execute the imaging of a target in the subject using the ultrasonic probe 30, thereby acquiring ultrasonic image data as the medical image data. Specifically, the acquiring function 171 acquires M-mode image data, B-mode image data, Doppler image data, and the like as the ultrasonic image data. Further, the acquiring function 171 includes a function of acquiring position data corresponding to the ultrasonic image data (e.g., position data of the ultrasonic probe 30 and position data of a cross-section based on the position of the ultrasonic probe 30).

For example, the acquiring function 171 acquires ultrasonic image data of multiple cross-sections as the medical image data of multiple cross-sections. Further, the acquiring function 171 acquires the position data corresponding to each of the ultrasonic image data of cross-sections. Hereinafter, a case where the acquiring function 171 acquires ultrasonic image data of the cross-sections will be described. The acquiring function 171 is one example of an acquiring unit.

In the embodiment, the ultrasonic image data of each cross-section acquired by the acquiring function 171 includes a data area that is visualized and a data-missing area that is not visualized and is difficult to make up for it. The data area means a range of an ultrasonic beam (raster) having a length that the transmitted wave can reach.

FIGS. 4A to 4G are diagrams for explaining the cause of the data-missing area when performing continuous imaging with the ultrasonic probe 30.

Figure 4A:
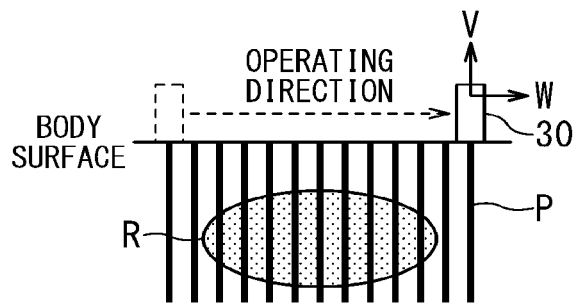
FIGS. 4A to 4G are diagrams for explaining the cause of a data-missing area when performing continuous imaging with the ultrasonic probe in the ultrasonic diagnostic apparatus as the example of the medical image diagnostic apparatus according to the embodiment.

FIG. 4A shows ideal data areas P when the ultrasonic probe 30 is operated in the positive direction of the W-axis. In FIG. 4A, the data area P is almost evenly spread over the entire target region R, and a data-missing area where the data area P does not exist does not appear. For example, the target is an organ and the target region is an organ region corresponding to the organ. In the embodiment, the organ is a unit that constitutes the body of an animal multicellular organism, and refers to an aggregation of tissues that cooperate to perform a certain function. The organ includes, for example, brain, heart, lung, liver, pancreas, stomach, intestine, blood vessel, nerve, and the like.

Figure 4B:
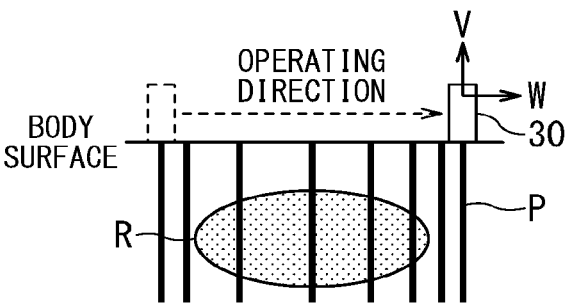

FIG. 4B shows each data area P in the case where the operation speed of the ultrasonic probe 30 in the positive direction of the W-axis is not constant with respect to FIG. 4A. In FIG. 4B, a data-missing area appears in which the data area P does not exist in the target region R where the space between the adjacent data areas P are relatively large.

Figure 4C:
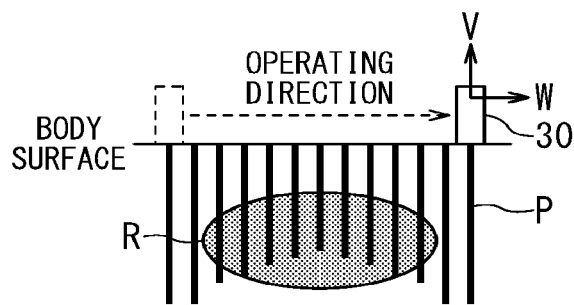

FIG. 4C shows each data area P in the case where a tissue having a large difference in acoustic impedance is included with respect to FIG. 4A. In FIG. 4C, in the target region R, a data-missing area appears in which the data area P does not exist in the central position on the negative side of the V-axis. In a tissue with a large difference in acoustic impedance, because the ultrasonic beam in the data area P is greatly attenuated, the length of the data area P passing through the tissue is shortened.

Figure 4D:
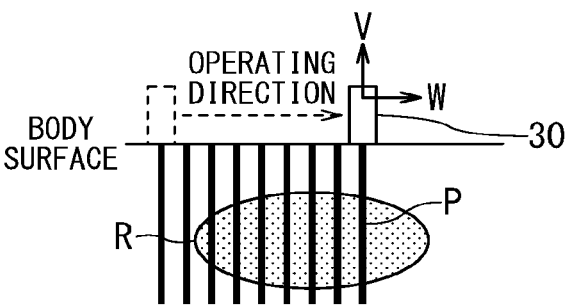

FIG. 4D shows each data area P in the case where imaging is stopped during the process of imaging the target region R corresponding to the target to be imaged, with respect to FIG. 4A. In FIG. 4D, in the target region R, a data-missing area appears where the data area P does not exist in a position on the positive direction side of the W-axis.

Figure 4E:
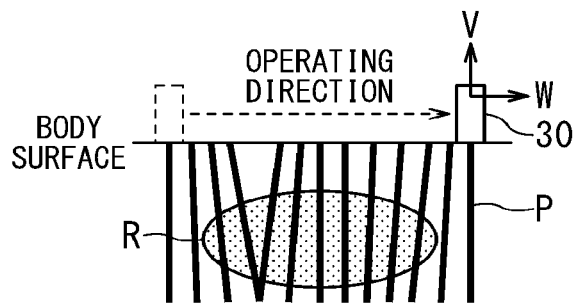

FIG. 4E shows each data area P in the case where the posture of the ultrasonic probe 30 during operation is not constant (the VW-axis rotates in the VW-plane) with respect to FIG. 4A. In FIG. 4E, in the target region R, a data-missing area appears in which the data area P does not exist in positions in the target region R where the space between the adjacent data areas P are relatively large.

Figure 4F:
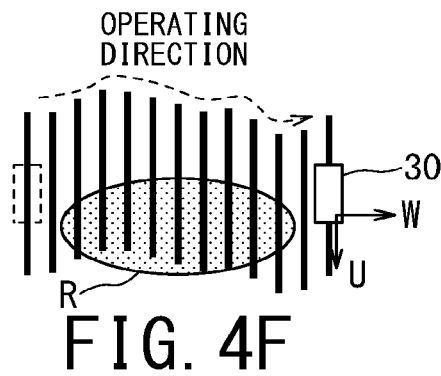

FIG. 4F shows each data area P in the case where the operation of the ultrasonic probe 30 is not linear (W-axis changes in the U-axis direction) with respect to FIG. 4A. In FIG. 4F, in the target region R, a data-missing area appears in which the data area P does not exist in a position on the positive direction side of the U-axis and on the negative direction side of the W-axis.

Figure 4G:
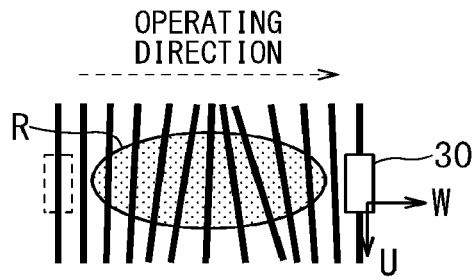

FIG. 4G shows each data area P in the case where the rotation angle of the ultrasonic probe 30 (UW-axis rotates in UW plane) during the operation is not constant with respect to FIG. 4A. In FIG. 4G, in the target region R, a data-missing area appears in which the data area P does not exist in positions where the space between the adjacent data areas P are relatively large.

In each of the cases shown in FIGS. 4B to 4G, a data-missing area appears where the data area P does not exist in the target region R as compared with the case of FIG. 4A.

Figure 5A:
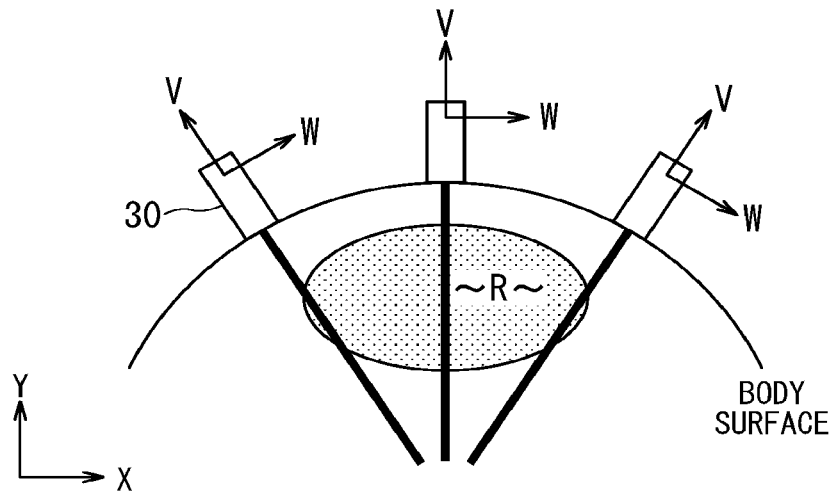
FIGS. 5A and 5B are diagrams for explaining the cause of a data-missing area when performing intermittent imaging with the ultrasonic probe in the ultrasonic diagnostic apparatus as the example of the medical image diagnostic apparatus according to the embodiment.
Figure 5B:
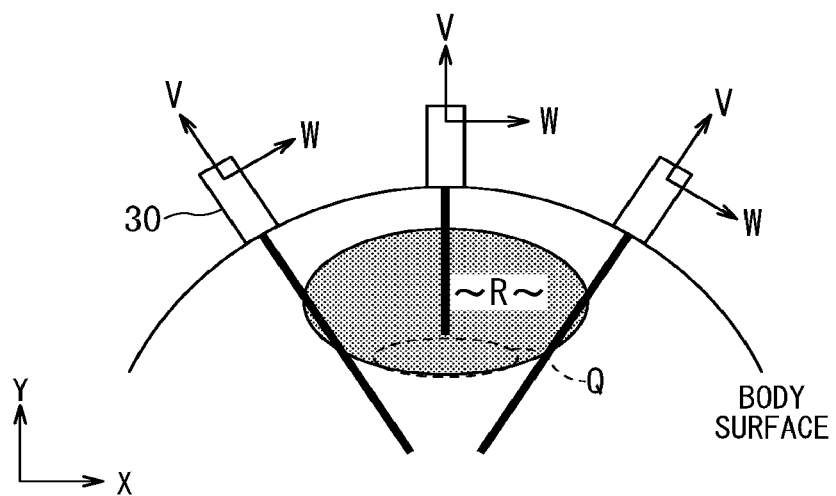

FIGS. 5A and 5B are diagrams for explaining the cause of the data-missing area when performing intermittent imaging with the ultrasonic probe 30.

FIG. 5A shows each data area P in the case where a tissue having a large difference in acoustic impedance is not included. FIG. 5B shows each data area P in the case where a tissue having a large difference in acoustic impedance is included with respect to FIG. 5A. In a tissue where the difference in acoustic impedance is large, because the ultrasonic beam in the data area P is greatly attenuated, the length of the data area P passing through the tissue is shortened.

In each of the left and right cases shown in FIG. 5B, the data-missing area appears in the target region R where the data area P does not exist because the data area P is shorter in comparison with the case of FIG. 5A. As a result, the unimaged target region Q appears in the target region R. Note that a region excluding the unimaged target region Q in the target region R is an imaged target region. That is, the target region R is composed of the unimaged target region Q and the imaged target region.

Note that the data-missing area also appears in a complicated manner by any combination of FIGS. 4B to 4G and 5B. As a result, in the target region R, the unimaged target region appears in a complicated manner.

Returning to the description of FIG. 3, the deriving function 172 has a function of deriving a target shape and an imaged target region in the subject from multiple ultrasonic image data and multiple position data acquired by the acquiring function 171. For example, the deriving function 172 includes a function of deriving an organ shape and the imaged organ region in the subject from the ultrasonic image data of multiple cross-sections and their position data. The deriving function 172 is one example of a deriving unit.

Further, the deriving function 172 arranges the ultrasonic image data acquired by the acquiring function 171 in the image memory 15 as the 3D memory on the basis of the position data acquired by the position sensor 40.

Figure 6A:
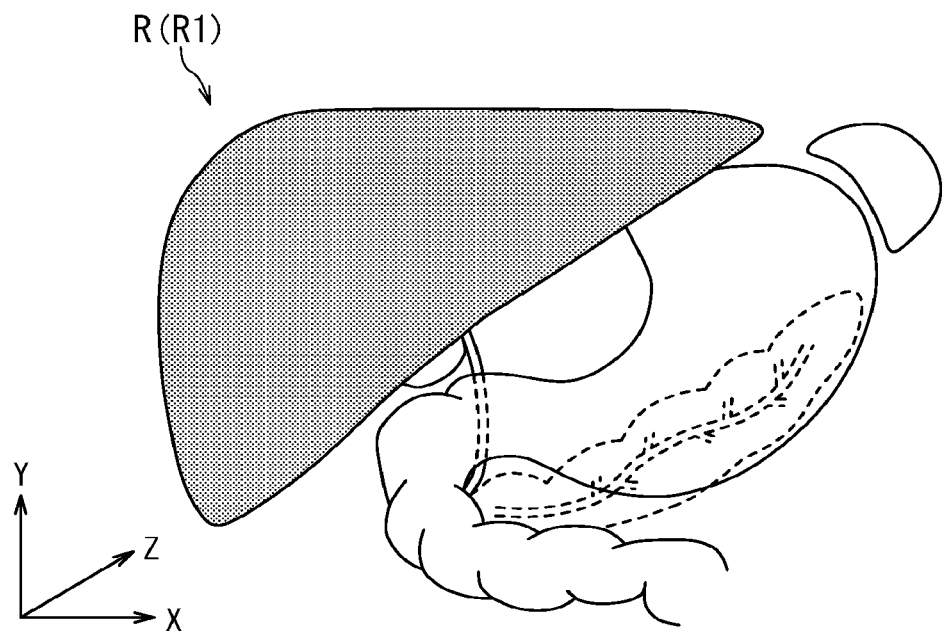
FIGS. 6A and 6B are diagrams showing the concept of the target in the subject and data areas included in ultrasonic image data of multiple cross-sections in the ultrasonic diagnostic apparatus as the example of the medical image diagnostic apparatus according to the embodiment.
Figure 6B:
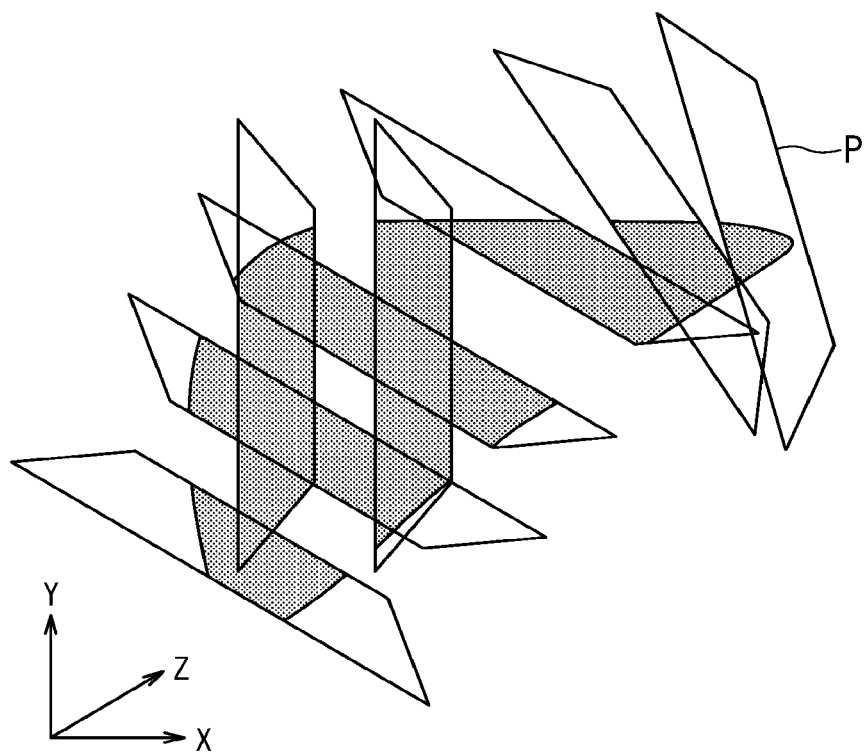

FIGS. 6A and 6B are diagrams showing the concept of the target in the subject and data areas P included in ultrasonic image data of multiple cross-sections.

FIG. 6A is a diagram showing a liver region R1 as a target region R acquired by transmitting and receiving ultrasonic waves to and from the liver which is the target in the subject. FIG. 6B shows data areas P when the ultrasonic probe 30 is applied to multiple positions on the body surface of the subject and the ultrasonic waves are transmitted and received to and from the multiple positions with respect to the liver shown in FIG. 6A.

As conceptually shown in FIG. 6B, even if ultrasonic waves are transmitted from any position of the liver R1 at any angle, the entire liver region R1 cannot be acquired as the data areas P that can be visualized. The gray portion shown in FIG. 6A but missing in FIG. 6B are the unimaged target region that appears due to data-missing. The data-missing occurs due to what has been described with reference to FIGS. 4A to 4G and FIGS. 5A and 5B.

Therefore, the deriving function 172 performs a process of deriving a shape of the organ such as the liver in the subject from the ultrasonic image data of cross-sections arranged three-dimensionally and from position data, thereby derives the organ shape and the imaged organ region. Then, the determining function 173, which will be described later, determines a region excluding the derived imaged organ region from the entire derived liver region R1 as an unimaged target region. The unimaged target region is a portion of the entire target region that cannot be visualized based on the data-missing area where the data areas P are insufficient. The unimaged target region means a region that should be continuously imaged in the present examination.

The deriving function 172 may use, for example, a database in which ultrasonic image data and an organ shape are associated with each other in the deriving process of the organ shape in the subject. The organ shape is further associated with not only the information indicating the general shape of the entire organ and the organ name but also: trajectory information indicating how to move the ultrasonic probe 30 to image the entire organ; various images acquired when the target organ was imaged in the past; and information regarding the position data of the various images. The deriving function 172 may use machine learning for the process of deriving the shape of the organ in the subject. Further, as machine learning, deep learning using a multilayer neural network such as CNN (Convolutional Deep Belief Network) and convolutional deep belief network (CDBN) may be used.

Hereinafter, an example of a case where the deriving function 172 includes the neural network Na, and where the entire organ shape included in the ultrasonic image data is derived from the partial organ shape included in the ultrasonic image data using deep learning will be described.

Figure 7:
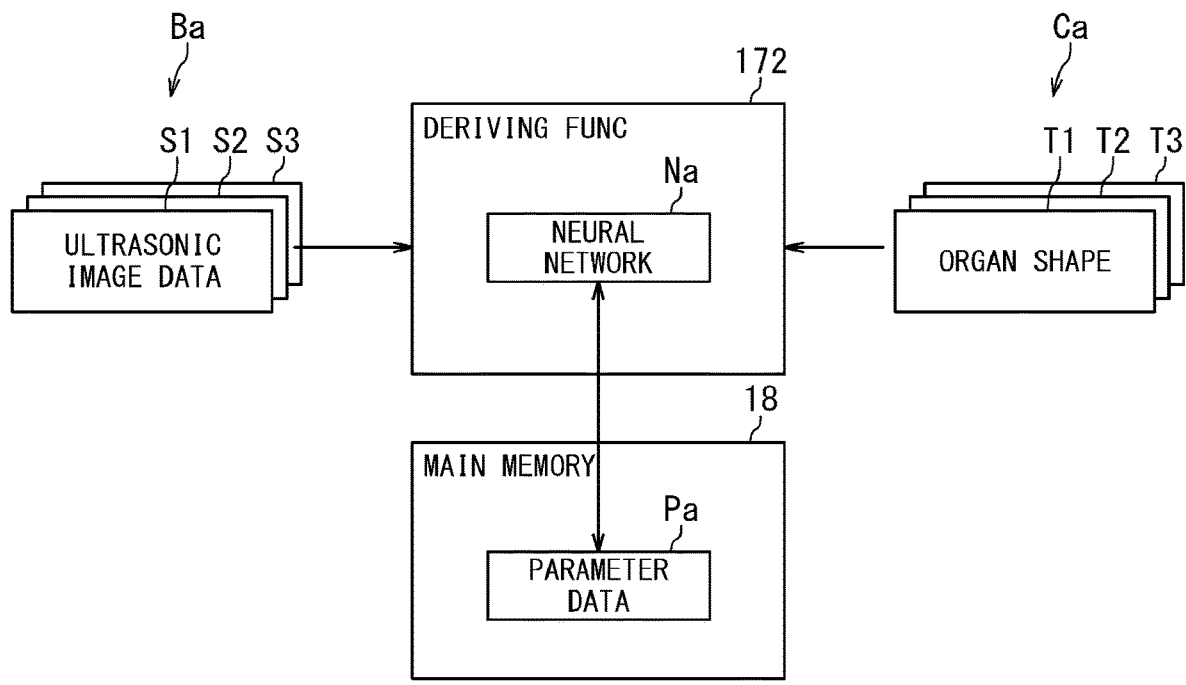
FIG. 7 is an explanatory diagram showing an example of a data flow during learning in the ultrasonic diagnostic apparatus as the example of the medical image diagnostic apparatus according to the embodiment.

FIG. 7 is an explanatory diagram showing an example of a data flow during learning.

The deriving function 172 inputs a large number of training data and performs learning to sequentially update the parameter data Pa. The training data is made up of a set of multiple ultrasonic image data (e.g., arbitrary cross-section data forming volume data) S1, S2, S3, . . . as training input data and organ shapes T1, T2, T3, . . . corresponding to each arbitrary cross-section data. The multiple ultrasonic image data S1, S2, S3, . . . constitutes a training input data group Ba. The organ shapes T1, T2, T3, . . . constitutes a training output data group Ca.

The deriving function 172 updates the parameter data Pa such that the result of processing the multiple ultrasonic image data S1, S2, S3, . . . by the neural network Na approaches the organ shapes T1, T2, T3, . . . every time the training data is input, that is so-called learning. Generally, when the rate of change of the parameter data Pa converges within the threshold value, the learning is determined to be completed. Hereinafter, the parameter data Pa after learning is particularly referred to as learned parameter data Pa'.

Figure 8:
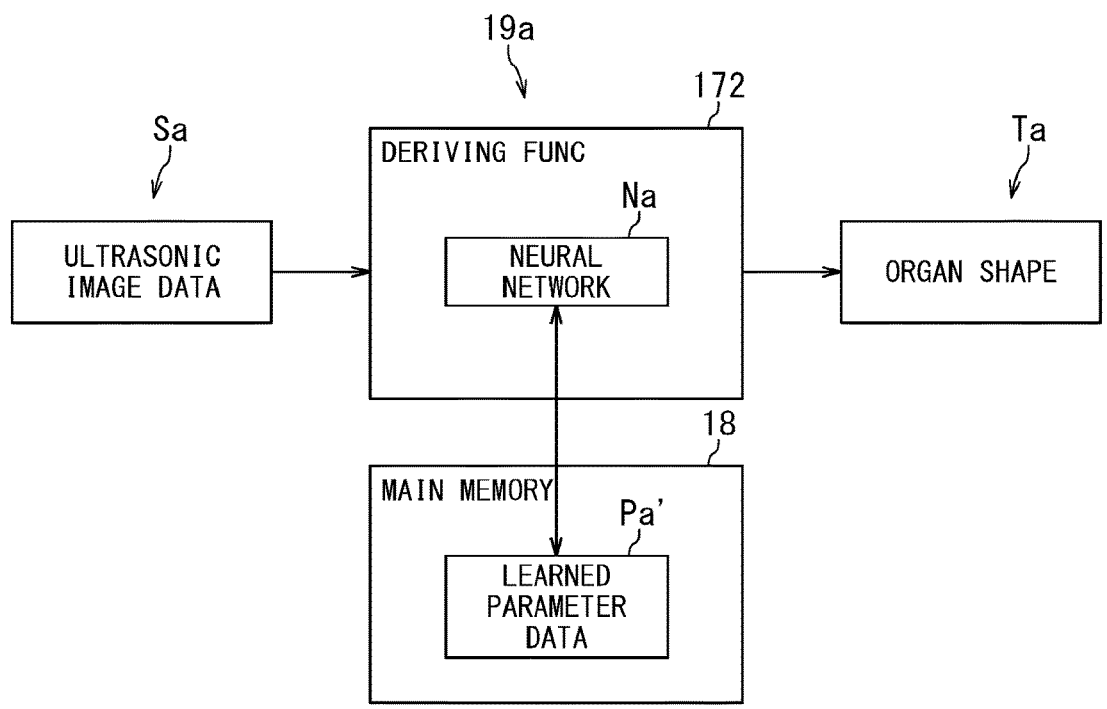
FIG. 8 is an explanatory diagram showing an example of a data flow during operation in the ultrasonic diagnostic apparatus as the example of the medical image diagnostic apparatus according to the embodiment.

Note that the type of training input data and the type of input data during operation shown in FIG. 8 should match. For example, if the input data during operation is ultrasonic image data, the training input data group Ba during learning should be ultrasonic image data as well.

The "ultrasonic image data" includes raw data generated by the ultrasonic diagnostic apparatus 1. That is, the input data of the neural network Na may be raw data before scan conversion.

FIG. 8 is an explanatory diagram showing an example of a data flow during operation.

In operation, the deriving function 172 inputs the ultrasonic image data Sa of the target to be diagnosed, and outputs the organ shape Ta included in the ultrasonic image data using the learned parameter data Pa'. When outputting the organ shape Ta, not only the shape and organ name of the entire organ but also any of: the current coordinate and angle of the ultrasonic probe; the motion of the ultrasonic probe 30 for imaging the unimaged target region, until the entire organ is imaged; and position data of each image in the entire organ may be output.

The neural network Na and the learned parameter data Pa' form a learned model 19a. The neural network Na is stored in the main memory 18 in the form of a program. The learned parameter data Pa' may be stored in the main memory 18 or may be stored in a storage medium connected to the ultrasonic diagnostic apparatus 1 via the network N. In this case, the deriving function 172 realized by the processor of the processing circuitry 17 reads the learned model 19a from the main memory 18 and executes it, thereby generates information on the organ shape included in the ultrasonic image data. The learned model 19a may be constructed by an integrated circuit such as an ASIC (Application Specific Integrated Circuit) and an FPGA (Field Programmable Gate Array).

Note that supplemental information may be used as input data in addition to the ultrasonic image data so as to improve the accuracy of determination by the deriving function 172. The supplementary information includes at least one of image data regarding the height and weight of the subject to be imaged, other modalities already imaged, and representative model data of gadget.

In this case, at the time of learning, the supplementary information of each subject of the multiple ultrasonic image data S1, S2, S3, . . . as the training input data is also input to the neural network Na as the training input data. At the time of operation, the deriving function 172 inputs the ultrasonic image data Ba of the target to be diagnosed and the supplemental information of the subject having the target to the learned model 19a read from the main memory 18, thereby outputs the organ shape Ta included in the ultrasonic image data. By using the ultrasonic image data and the supplementary information of the subject as the input data, it is possible to generate the learned parameter data Pa' that has been learned according to the type of the subject. Therefore, it is possible to improve the deriving accuracy as compared with the case where only the ultrasonic image data is used as the input data.

Returning to the description of FIG. 3, the determining function 173 has a function of determining an unimaged target region based on the ultrasonic image data of cross-sections and the position data acquired by the acquiring function 171. The unimaged target region is a region of the target that is not included in the ultrasonic image data of the cross-sections. Alternatively, the determining function 173 has a function of determining an unimaged target region (e.g., unimaged organ region) on the basis of the target shape (e.g., organ shape) derived by the deriving function 172 and the imaged target region (e.g., organ region). That is, the determining function 173 three-dimensionally compares the imaged organ shape included in the ultrasonic image data with the derived organ shape, thereby determines the unimaged organ region resulting from data-missing in the organ region. The determining function 173 is one example of a determining unit.

The output control function 174 has a function of outputting the three-dimensional information of the unimaged target region determined by the determining function 173 and/or information for imaging the unimaged target region to the outside of the processing circuitry 17. For example, the output control function 174 includes a display control function 71, a storage control function 72, and a transmission control function 73. The output control function 174 may include at least one of the display control function 71, the storage control function 72, and the transmission control function 73.

The display control function 71 has a function of displaying the ultrasonic image data acquired by the acquiring function 171 on the display 20, and a function of displaying information regarding an unimaged target region when the unimaged target region is determined by the determining function 173 on the display 20. For example, the information regarding the unimaged target region is the coordinate (shown as a marker) of the ultrasonic probe 30 on the body surface, the angle, and the pressure at the time of imaging. The coordinate of the ultrasonic probe 30 on the body surface is a display of the unimaged organ region (position/size) with respect to the entire organ, and is necessary to image the unimaged organ region. An alert can be displayed together with the display of an unimaged organ region. The coordinate of the ultrasonic probe 30 on the body surface may be directly projected on the body surface. The display control function 71 is one example of a display control unit.

The storage control function 72 has a function of storing the three-dimensional information of the unimaged target region and the information for imaging in the storage medium such as image memory 15 when the unimaged target region is determined by the determining function 173. The storage control function 72 is one example of a storage control unit.

The transmission control function 73 has a function of transmitting the three-dimensional information of the unimaged target region and the information for imaging to an outside apparatus (e.g., the medical image display apparatus 80 shown in FIG. 13) of the medical image processing apparatus 10 via the network interface 16 when the unimaged target region is determined by the determining function 173. The transmission control function 73 is one example of a transmission control unit.

The moving control function 175 has a function of controlling an external device such as a robot arm when the unimaged target region is determined by the determining function 173, thereby moving (including slide movement, rotation movement, probe posture angle, and probe pressure change) the ultrasonic probe 30 which is the scanner. The moving operation of the ultrasonic probe 30 may be operated by an operator who holds the ultrasonic probe 30, may be performed by an auto scan performed for the purpose of correcting movement of the subject such as respiratory characteristics, or may be performed by the robot arm scan for the purpose of reducing the operation of the ultrasonic probe 30 by the operator. The moving control function 175 is one example of a moving control unit.

Subsequently, the operation of the ultrasonic diagnostic apparatus 1 will be described with reference to FIGS. 9 and 12.

Figure 9:
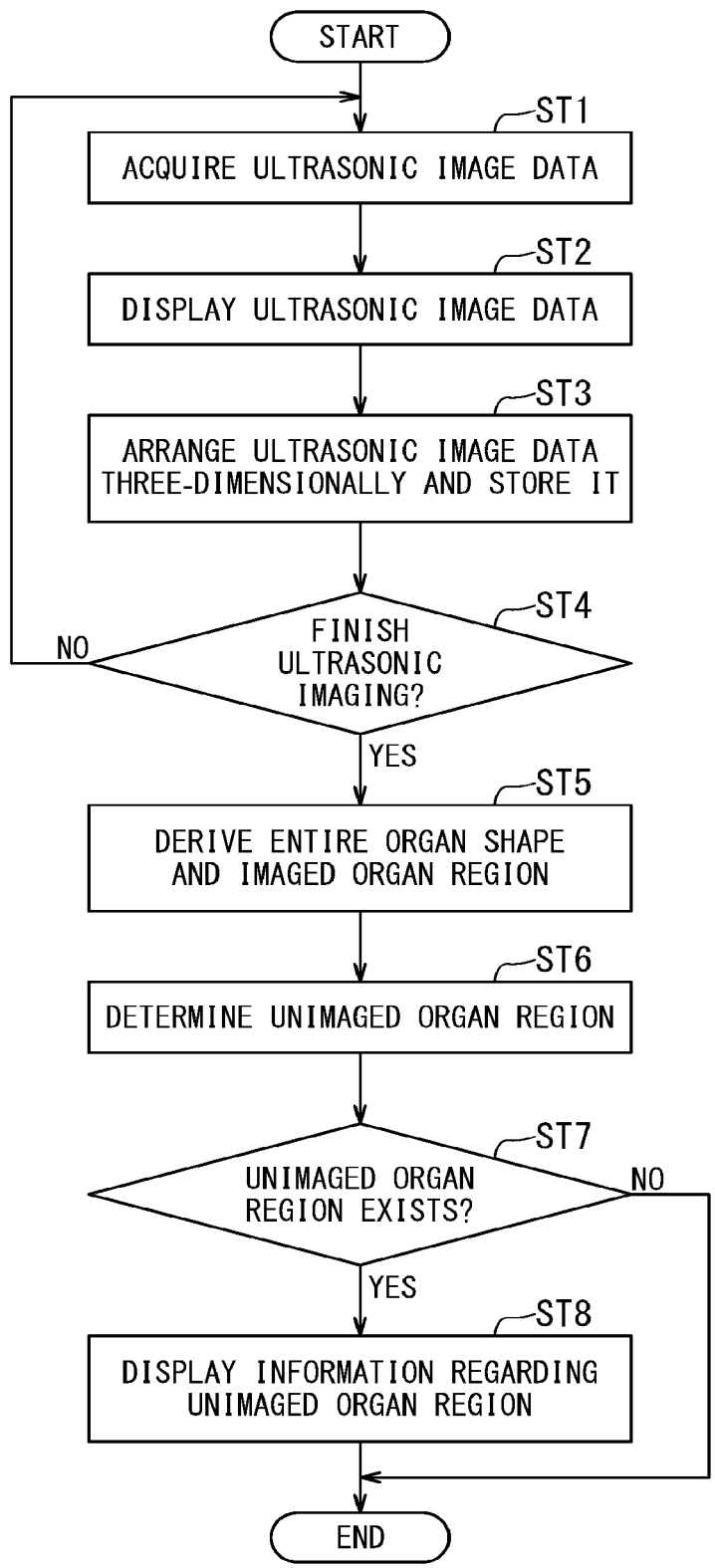
FIG. 9 is a diagram showing a first operation example of the ultrasonic diagnostic apparatus as a flowchart, the apparatus being the example of the medical image diagnostic apparatus according to the embodiment.

FIG. 9 is a diagram showing a first operation example of the ultrasonic diagnostic apparatus 1 as a flowchart. In FIG. 9, reference numerals in which "ST" is attached to numbers indicate steps in the flowchart. In addition, in FIG. 9, a case where the target to be imaged is an organ will be described.

The acquiring function 171 controls the T/R circuit 11, the B-mode processing circuit 12, the Doppler processing circuit 13, the image generating circuit 14, and the like and executes the ultrasonic imaging of the target in the subject using the ultrasonic probe 30, thereby acquires ultrasonic image data (step ST1). The display control function 71 displays the ultrasonic image data acquired in step ST1 as an ultrasonic image on the display 20 (step ST2).

Further, the acquiring function 171 stores the ultrasonic image data acquired in step ST1 in a three-dimensional arrangement in the 3D memory of the image memory 15 on the basis of the position data of the ultrasonic image data (step ST3). The position sensor 40 is not an indispensable component because the relative change in the coordinate and posture of the ultrasonic probe 30 can be detected by matching the data area in which the data to be visualized exists. The display control function 71 may display the three-dimensional arrangement of ultrasonic image data on the display 20. As a result, the operator who takes an image can visually recognize the range of the image taken in the body, particularly in the trunk.

The acquiring function 171 determines whether to finish the ultrasonic imaging (step ST4). The acquiring function 171 may determine to finish the ultrasonic imaging on the basis of the finish instruction input by the operator via the input interface 19, or may determine that the ultrasonic imaging is finished if the ultrasonic probe 30 is in the air apart from the body surface of the subject after a certain time elapsed. For example, whether the ultrasonic probe 30 is in the air may be determined based on the position data of the ultrasonic probe 30.

If it is determined as "NO" in step ST4, that is, if it is determined that the ultrasonic imaging for the next cross-section will be performed without finishing ultrasonic imaging, the acquiring function 171 controls the T/R circuit 11, the B-mode processing circuit 12, the Doppler processing circuit 13, the image generating circuit 14, etc., executes the ultrasonic imaging using the ultrasonic probe 30, thereby acquires ultrasonic image data for the next cross-section (step ST1). By repeating the set of steps ST1 to ST3 based on "NO" in step ST4, ultrasonic image data of cross-sections is arranged in the 3D memory of the image memory 15 (shown in FIG. 6B).

On the other hand, if it is determined as "YES" in step ST4, that is, if it is determined that the ultrasonic imaging is to be finished, the deriving function 172 derives the organ shape of the entire target organ in the subject and the imaged organ region on the basis of the ultrasonic image data of one or multiple cross-sections arranged in the 3D memory of the image memory 15 (step ST5). The determining function 173 determines a three-dimensional unimaged organ region on the basis of the partial organ shape included in the ultrasonic image data of one or multiple cross-sections arranged three-dimensionally in step ST3 and the entire organ shape derived in step ST5 (step ST6).

The determining function 173 extracts an organ contour from ultrasonic image data of cross-sections arranged three-dimensionally, arranges the extracted organ contour in a three-dimensional manner, and collates the arranged one with a 3D model of the entire organ. Then, the determining function 173 determines, as an unimaged organ region, a region acquired by removing the organ contour included in the already existing data area from the organ contour of the 3D model. Note that the 3D model may be generated by acquiring the organ contour from volume data such as 3D-CT image data acquired in advance from the same subject (same patient), or may be a 3D model showing a general organ shape.

The determining function 173 determines whether or not there is an unimaged organ region (step ST7). If it is determined as "YES" in step ST7, that is, if it is determined that there is the unimaged organ region, the display control function 71 displays information regarding the unimaged organ region on the display 20 for the operator (step ST8). The information regarding the unimaged organ region may be the range of the ultrasonic beam determined to fill the unimaged organ region (display example (1) described below), or may include the body surface coordinate and posture (display examples (2) to (4) described later) of the ultrasonic probe 30 for imaging an unimaged organ region. Further, the display control function 71 displays the information for imaging the unimaged target region, thereby displaying the information regarding the unimaged target region, and/or three-dimensionally displays the unimaged target region.

Figure 10:
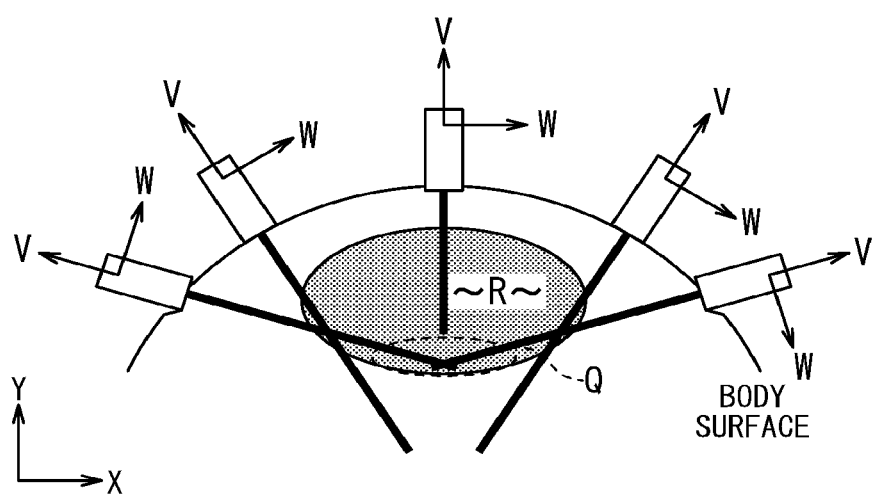
FIG. 10 is a diagram for explaining a method of determining the body surface coordinate and posture of the ultrasonic probe for imaging the unimaged organ region due to data-missing in the ultrasonic diagnostic apparatus as the example of the medical image diagnostic apparatus according to the embodiment.

FIG. 10 is a diagram for explaining a method of determining the body surface coordinate and posture of the ultrasonic probe 30 for imaging the unimaged organ region due to data-missing.

FIG. 10 shows the unimaged target region Q shown in FIG. 5B. In the case of ultrasonic imaging, the display control function 71 may select one having a similar imaging area, imaging position, and imaging angle to the already existing data area P in body surface coordinate and posture that can image the unimaged target region Q in the shallowest possible area (e.g., two probe coordinates at both ends in FIG. 10). The display control function 71 may select the body surface coordinate and posture of the ultrasonic probe 30 displayed for imaging the unimaged target region. Note that the body surface coordinate and posture selected may be one or more. Further, when the position of an anatomy (for example, bone) where the difference in acoustic impedance in the subject is large is known, the body surface coordinate and posture where the anatomy does not have a large difference in acoustic impedance on the cross-section determined by the body surface coordinate and posture can be selected, or the body surface coordinate and posture can be adjusted by shifting the body surface coordinate and posture.

The information regarding the unimaged target region will be shown in the following display examples (1) to (4).
  (1) A range of the ultrasonic beam determined to fill the unimaged target region (shown in FIG. 6B) on the 3D model is displayed.
  (2) A probe mark of the ultrasonic probe 30 for imaging an unimaged target region is projected and displayed on the subject.
  (3) A probe mark of the ultrasonic probe 30 for imaging the unimaged target region is displayed on the 3D model of the subject.
  (4) An LED lamp or the like is attached to the ultrasonic probe 30 itself, and the moving and rotating directions are displayed by the lamp.

Each of FIGS. 11A to 11C is a diagram showing a display example of information regarding the unimaged target region due to data-missing.

FIG. 11A shows the above display example (1). FIG. 11B shows the above display example (2). FIG. 11C shows the above display example (3). In FIG. 11A, the top side of the trapezoid formed by a thick line (the shorter side of the two sides) corresponds to the body surface coordinate. In FIG. 11B, the mark M1 is a probe mark projected on the body surface of the subject, and the mark M2 is a mark of a marker which is projected on the body surface of the subject and is attached to one side surface of the ultrasonic probe 30. In FIG. 11C, the mark M1 is a probe mark on the 3D model displayed on the display 20, and the mark M2 is mark of a marker attached to one side surface of the ultrasonic probe 30 on the 3D model displayed on the display 20.

Note that the unimaged target region may be projected with the marks M1 and M2 on the body surface of the subject. The position of the unimaged target region is acquired based on the multiple ultrasonic image data including the imaged target region and their position data. This is because it is possible to acquire the position of the entire target region based on the multiple ultrasonic image data including the imaged target region and their position data.

The operator confirms the information regarding the unimaged target region displayed in step ST8, and continues the examination if necessary. Specifically, the operator presses the tip of the ultrasonic probe 30 to the body surface position of the subject corresponding to the body surface position of the subject displayed on the display 20 (top side of the trapezoid). Alternatively, the operator presses the tip of the ultrasonic probe 30 against the mark M1 (shown in FIG. 11B) such that the marker matches the mark M2 (shown in FIG. 11B) projected on the body surface of the subject. Alternatively, the operator presses the tip of the ultrasonic probe 30 against the mark M1 (shown in FIG.

11C) such that the marker matches the mark M2 (shown in FIG. 11C) at the body surface position of the subject displayed on the display 20. The operator presses the ultrasonic probe 30 to match the markers attached to the ultrasonic probe 30 so as to match the position of the ultrasonic probe 30 in the rotation direction.

Further, it is possible to display a probe model for imaging the unimaged target region on the 3D model of the subject, thereby display the direction in which the ultrasonic probe 30 should be moved and rotated with respect to the probe model by an arrow. Note that the unimaged target region may be displayed on the probe model with an arrow.

Returning to the description of FIG. 9, if it is determined as "NO" in step ST7, that is, if it is determined that there is no unimaged organ region, the examination is finished.

As described above, according to the first operation example of the ultrasonic diagnostic apparatus 1, when the data-missing occurs due to insufficient imaging, it is possible to encourage the operator after the imaging to perform additional imaging of the unimaged target region due to data-missing. Further, it is also possible to present the operator with information regarding the unimaged target region. For example, it is possible to display the unimaged target region itself as the information regarding the unimaged region, or to display which coordinate and posture the ultrasonic probe 30 should be applied to on the body surface of the subject. Further, it does not rely on complementation using other images to make up for the unimaged target region. As a result, it is possible to avoid a situation that additional imaging should be performed on the unimaged target region is determined after the subject leaves the room after the examination.

FIG. 12 is a diagram showing a second operation example of the ultrasonic diagnostic apparatus 1 as a flowchart. In FIG. 12, the reference numerals in which "ST" is attached to numbers indicate the steps of the flowchart. The second operation example of the ultrasonic diagnostic apparatus 1 is different from the first operation example of the ultrasonic diagnostic apparatus 1 that the unimaged target regions is determined sequentially. In addition, in FIG. 12, a case where the target to be imaged is an organ will be described.

In the FIG. 12, the same steps as those shown in FIG. 9 are designated by the same reference numerals, and the description thereof will be omitted.

The deriving function 172 derives the organ shape of the entire target organ in the subject and the imaged organ region from the ultrasonic image data of one or multiple cross-sections arranged in the 3D memory of the image memory 15, as in step ST5 shown in FIG. 9 (step ST15). The determining function 173 determines a three-dimensional unimaged organ region on the basis of the ultrasonic image data of one or multiple cross-sections arranged in the 3D memory of the image memory 15, as in step ST6 shown in FIG. 9 (step ST16).

The display control function 71 determines whether or not the ratio of the volume or contour of the unimaged organ region to the volume or contour of the entire organ shape derived in step ST15 is equal to or less than a threshold value (e.g. 20%). If it is determined as "YES" in step ST17, that is, if it is determined that the volume or contour ratio of the unimaged organ region is less than or equal to the threshold value, the display control function 71 displays on the display 20 that the data is sufficient with only a little missing data (step ST18).

On the other hand, if it is determined as "NO" in step ST17, that is, if it is determined that the ratio of the volume of the unimaged organ region exceeds the threshold value, the display control function 71 displays on the display 20 information regarding the unimaged organ region for the operator, as in step ST8 shown in FIG. 9 (step ST19).

As described above, according to the second operation example of the ultrasonic diagnostic apparatus 1, it is possible to present the operator the ratio of the volume or contour of the unimaged target region to the volume or contour of acquired from the entire derived target shape and with its coordinate and range in real time during imaging. As a result, it is possible to for the operator to proceed with imaging while confirming the ratio of the unimaged target region. Therefore, it is possible to avoid a situation in which it is determined that additional imaging should be performed on the unimaged target region after the subject disappears after the examination.

Note that the data-missing due to insufficient imaging is described, but the present invention is not limited to this case. For example, the present invention can be applied to the case where there is an artifact on the ultrasonic image data and a part of the tissue to be visually recognized cannot be visually recognized even if it is not the data-missing. In this case, the artifact portion on the ultrasonic image data can be detected and set the portion as the data-missing area.

After the unimaged target region is determined, virtual ultrasonic image data may be displayed as a model assuming that the unimaged target region is imaged. The virtual ultrasonic image data may be generated by synthesizing pixel values at positions close to the unimaged target region in the already existing data area, or may be an MPR image generated from the volume data when the CT image volume data and the like already exist.

2. First Modification

The target in the subject imaged by the ultrasonic probe 30 may be an abnormal target. For example, the target in the subject to be imaged may be a target including a tumor. In this case, the deriving function 172 derives the target shape and the imaged target region in the same subject from ultrasonic image data of cross-sections to be imaged and their position data on the basis of the past medical image data (for example, ultrasonic image data) of the same subject. Then, the determining function 173 determines an unimaged target region based on the target shape derived by the deriving function 172 and the imaged target region. The determining function 173 can extract the position of the tumor based on the past medical image data, or can determine the position of the data area based on the position data of the ultrasonic image data of the cross-sections to be imaged.

As a result, when the tumor part is not imaged, the output control function 174 outputs three-dimensional information of the unimaged target region including the tumor determined by the determining function 173 or information for imaging the unimaged target region including the tumor to the outside of the processing circuitry 17.

On the other hand, when the tumor target has been imaged, the determining function 173 determines the degree of data-missing in the tumor of the imaged target region. When it is determined that the degree of data-missing in the tumor is greater than or equal to the threshold value, the output control function 174 outputs information for imaging the tumor in the imaged target region to the outside of the processing circuitry 17. The display example of the information for imaging the tumor is the same as the above mentioned "display examples (1) to (4) of the information regarding the unimaged target region". As a result, it is possible to encourage the operator to reimage the tumor at a fine interval or from a suitable direction. If the degree of data-missing in the tumor is less than the threshold value and it is determined that the data related to the tumor is sufficient, the output control function 174 allows to finish of ultrasonic imaging.

3. Second Modification

A case where the transmission control function 73 of the output control function 174 outputs the three-dimensional information of the unimaged target region determined by the determining function 173 and/or the information for imaging the unimaged target region to the external apparatus of the ultrasonic diagnostic apparatus 1 will be described.

FIG. 13 is a schematic diagram showing a configuration of a medical image system including the ultrasonic diagnostic apparatus as an example of a medical image diagnostic apparatus according to the second modification.

FIG. 13 shows a medical image system S including the ultrasonic diagnostic apparatus 1 as the medical image diagnostic apparatus. The medical image system S includes the ultrasonic diagnostic apparatus 1 described above and a medical image display apparatus 80 as a medical image processing apparatus. The medical image display apparatus 80 is a workstation that performs various types of image processing on medical image data, a portable information processing terminal such as a tablet terminal, or the like, and is connected to the ultrasonic diagnostic apparatus 1 so as to be communicable via the network N.

The medical image display apparatus 80 includes a network interface 86, processing circuitry 87, a memory 88, an input interface 89, and a display 90. The network interface 86, the processing circuit 87, the memory 88, the input interface 89, and the display 90 have the same configurations as those of the network interface 16, the processing circuitry 17, the main memory 18, the input interface 19, and the display 20 shown in FIG. 1, respectively, which description will be omitted.

The processing circuitry 87 reads and executes a computer program stored in the memory 88 or directly incorporated in the processing circuitry 87, thereby realizes a display control function 71A. Hereinafter, the case where the function 71A functions as software will be described as an example, but all or part of the function 71A may be provided in the medical image display apparatus 80 as a function of the circuit such as the ASIC.

The display control function 71A includes a function of receiving the ultrasonic image data acquired by the acquiring function 171 of the ultrasonic diagnostic apparatus 1 and displaying such data on the display 90, and a function of receiving the information regarding the unimaged target region and displays it on the display 90 when the unimaged target region is determined by the determining function 173 of the ultrasonic diagnostic apparatus 1. The display control function 71A may also generate 3D hologram image data (stereoscopically visible image data), display it on a 3D hologram display as the display 90, and project it on the body surface of the subject.

With the configuration shown in FIG. 13, the medical image display apparatus 80, which is the external apparatus of the ultrasonic diagnostic apparatus 1, is possible to display three-dimensional information of the unimaged target region and/or the information for imaging the unimaged target region.

According to at least one embodiment described above, it is possible to determine the unimaged target region in medical image data. In addition, it is possible to reduce the insufficient imaging, thereby reduce differences between operators and improve efficiency.

Further, in the above-described embodiment, the case where the organ in the subject is the main target that the imaged organ region and the unimaged organ region are determined has been described. However, the organ is merely an example of the target, and the same determination may be performed on the target other than the organ in the subject. For example, the target may be a surgical device such as a stent inserted in the subject instead of the organ, or may be a lesion such as a tumor or lymphoma, or a layer of muscle. The shape of the target to be imaged may be collectively referred to as "target shape". The imaged region may be referred to as "imaged target region". The unimaged region may be referred to as "unimaged target region".

While certain embodiments have been described, these embodiments have been presented by way of example only, and are not intended to limit the scope of the inventions. Indeed, the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising:
   processing circuitry configured to
      sequentially acquire cross sectional medical images of a target of a subject acquired by performing an imaging of the target by scanning with a scanner, and position data of the acquired cross sectional medical images,
      automatically determine, based on the acquired cross sectional medical images and the acquired position data, an unimaged region being a part of the target, the unimaged region being included in a data-missing area, which has a size equal to or larger than a threshold, and which appears between adjacent cross sectional medical images of the acquired cross sectional medical images, and
      automatically move the scanner such that the unimaged region within the target is scanned when the unimaged region is determined.

2. The medical image diagnostic apparatus according to claim 1, wherein
   the processing circuitry is configured to further display information regarding the unimaged region when the unimaged region is determined.

3. The medical image diagnostic apparatus according to claim 2, wherein
   the processing circuitry is configured to display the information regarding the unimaged region after the imaging is completed.

4. The medical image diagnostic apparatus according to claim 2, wherein
   the processing circuitry is configured to display the information regarding the unimaged region during imaging.

5. The medical image diagnostic apparatus according to claim 2, wherein
   the processing circuitry is configured to display the unimaged region three-dimensionally or display information for imaging the unimaged region, thereby displaying the information regarding the unimaged region.

6. The medical image diagnostic apparatus according to claim 2, wherein
   the processing circuitry is configured to project the unimaged region and a position for imaging the unimaged region on the target, thereby displaying the information regarding the unimaged region.

7. The medical image diagnostic apparatus according to claim 2, wherein
the processing circuitry is configured to display the unimaged region and a position for imaging the region on a three-dimensional model as the information regarding the unimaged region.

8. The medical image diagnostic apparatus according to claim 1, wherein
the processing circuitry is configured to
derive a target shape of the subject and an imaged region of the target included in the acquired cross sectional medical images from the acquired cross sectional medical images and position data thereof, and
determine the unimaged region based on the derived target shape and imaged region.

9. The medical image diagnostic apparatus according to claim 1, wherein
the processing circuitry is further configured to move a scanner when the unimaged region is determined.

10. The medical image diagnostic apparatus according to claim 1, wherein
the processing circuitry is further configured to store, in a storage medium, information for imaging with a three-dimensional information regarding the unimaged region, and/or transmit the information for imaging with the three-dimensional information regarding the unimaged region to an outside of the medical image diagnostic apparatus.

11. The medical image diagnostic apparatus according to claim 1, wherein
the processing circuitry is configured to
sequentially acquire the cross sectional medical images of an organ which is the target, acquired by performing an imaging of the organ, and
automatically determine, based on the acquired cross sectional medical images and the acquired position data, an unimaged region being a part of the organ, which is not included in the acquired cross sectional medical images.

12. The medical image diagnostic apparatus according to claim 1, wherein
the processing circuitry is configured to
three-dimensionally arrange the acquired cross sectional medical images based on the position data thereof,
derive the target and an imaged region of the target included in the arranged cross sectional medical images based on the arranged cross sectional medical images and the position data thereof, and
automatically determine the unimaged region based on the derived target and imaged region.

13. The medical image diagnostic apparatus according to claim 1, wherein the data-missing area further appears on: (a) a deep side of a short-depth cross sectional medical image of the acquired cross sectional medical images in a depth direction; (b) a side where there is no cross sectional medical image adjacent to an edge cross sectional medical image of the acquired cross sectional medical images; or (c) a side of any of the acquired cross sectional medical images in a direction orthogonal to the depth direction and a moving direction of the scanner.

14. A ultrasonic diagnostic apparatus comprising:
processing circuitry configured to
sequentially acquire cross sectional ultrasonic images of a target of a subject acquired by performing an imaging of the target by scanning with an ultrasonic probe, and position data of the acquired cross sectional ultrasonic images,
automatically determine, based on the acquired cross sectional ultrasonic images and the acquired position data, an unimaged region being a part of the target, the unimaged region being included in a data-missing area, which has a size equal to or larger than a threshold, and which appears between adjacent cross sectional medical images of the acquired cross sectional medical images, and
automatically move the ultrasonic probe such that the unimaged region within the target is scanned when the unimaged region is determined.

15. The ultrasonic diagnostic apparatus according to claim 14, wherein
the processing circuitry is configured to
derive a target shape of the subject and an imaged region of the target included in the acquired cross sectional ultrasonic images from the acquired cross sectional medical images and position data thereof, and
determine the unimaged region based on the derived target shape and imaged region.

16. A medical image system in which a medical image diagnostic apparatus and a medical image processing apparatus are communicably connected via a network, comprising:
processing circuitry configured to
sequentially acquire cross sectional medical images of a target of a subject acquired by performing an imaging of the target by scanning with a scanner, and position data of the acquired cross sectional medical images,
automatically determine, based on the acquired cross sectional medical images and the acquired position data, an unimaged region being a part of the target, the unimaged region being included in a data-missing area, which has a size equal to or larger than a threshold, and which appears between adjacent cross sectional medical images of the acquired cross sectional medical images, and
automatically move the scanner such that the unimaged region within the target is scanned when the unimaged region is determined.

17. The medical image system apparatus according to claim 16, wherein the processing circuitry is further configured to
derive a target shape of the subject and an imaged region of the target included in the acquired cross sectional medical images from the acquired cross sectional medical images and position data thereof, and
determine the unimaged region based on the derived target shape and imaged region.

18. An imaging control method comprising:
sequentially acquiring cross sectional medical images of a target of a subject acquired by performing an imaging of the target by scanning with a scanner, and position data of the acquired cross sectional medical images;
automatically determining, based on the acquired cross sectional medical images and the acquired position data, an unimaged region being a part of the target, the unimaged region being included in a data-missing area, which has a size equal to or larger than a threshold, and which appears between adjacent cross sectional medical images of the acquired cross sectional medical images; and automatically moving the scanner such that the unimaged region within the target is scanned when the unimaged region is determined.

19. The imaging control method according to claim 18, further comprising:

deriving a target shape of the subject and an imaged region of the target included in the acquired cross sectional medical images from the acquired cross sectional medical images and position data thereof, and determining the unimaged region based on the derived target shape and imaged region.

\* \* \* \* \*